United States Patent
Sakamoto et al.

(10) Patent No.: US 11,220,665 B2
(45) Date of Patent: Jan. 11, 2022

(54) PRODUCTION METHOD OF FILAMENTOUS FUNGUS PELLET

(71) Applicant: KAO CORPORATION, Tokyo (JP)

(72) Inventors: Takeshi Sakamoto, Wakayama (JP); Yutaka Irie, Wakayama (JP)

(73) Assignee: KAO CORPORATION, Tokyo (JP)

(*) Notice: Subject to any disclaimer, the term of this patent is extended or adjusted under 35 U.S.C. 154(b) by 8 days.

(21) Appl. No.: 16/618,075

(22) PCT Filed: May 29, 2018

(86) PCT No.: PCT/JP2018/020443
§ 371 (c)(1),
(2) Date: Nov. 27, 2019

(87) PCT Pub. No.: WO2018/221482
PCT Pub. Date: Dec. 6, 2018

(65) Prior Publication Data
US 2020/0165562 A1 May 28, 2020

(30) Foreign Application Priority Data
May 30, 2017 (JP) .............................. JP2017-106360

(51) Int. Cl.
*C12P 7/06* (2006.01)
*C12P 7/46* (2006.01)
*C12N 1/14* (2006.01)

(52) U.S. Cl.
CPC ................ *C12N 1/14* (2013.01); *C12P 7/065* (2013.01); *C12P 7/46* (2013.01)

(58) Field of Classification Search
CPC ... C12N 1/14; C12N 1/38; C12P 7/065; C12P 7/46; C12P 7/40; C12P 7/56; Y02E 50/10
See application file for complete search history.

(56) References Cited

U.S. PATENT DOCUMENTS

| 3,821,086 A | 6/1974 | Lee et al. | |
|---|---|---|---|
| 2015/0125915 A1* | 5/2015 | Tsuboi | C12N 1/14 435/139 |

FOREIGN PATENT DOCUMENTS

| JP | 48-18487 A | 3/1973 |
|---|---|---|
| JP | 6-253871 A | 9/1994 |

OTHER PUBLICATIONS

Zhang et al., Critical Reviews in Biotechnology 36(6):1066-1077, published online Sep. 16, 2015.*
Fakhrullin et al., Langmuir 25(8):4628-4634, 2009.*
"The 48th Meeting of the Society of Chemical Engineers of Japan", poster session LQ268, (Tokushima, 2016), total of 3 pages.
Byrne et al., "Effect of Polymers on Pelleting of Rhizopus Arrhizus", Trans. Br. mycol. Soc., 1987, vol. 89, No. 3, pp. 367-371, ISSN 0007-1536, entire text.
Byrne et al., "Growth of Rhizopus arrhizus in fermentation media", Journal of Industrial Microbiology, 4, pp. 155-161 (1989).
El-Enshasy, "Production of Gluconic Acid by Free and Immobilized Cells of Recombinant Aspergillus niger in Batch and Repeated Batch Cultures", Deutsche Lebensmittel-Rundschau, 2003, vol. 99, pp. 409-415, ISSN 0012-0413, Materials and Methods, table 2.
Elmayergi, "Mechanisms of Pellet Formation of Aspergillus niger with an Additive", J. Ferment. Technol., 1975, vol. 53, No. 10, pp. 722-729, ISSN 0367-5963, Materials and Methods, table 3.
Fu et al., "Effects of Pellet Characteristics on L-Lactic Acid Fermentation by R. oryzae: Pellet Morphology, Diameter, Density, and Interior Structure", Apply Biochem. Biotechnol., vol. 174, 2014, pp. 2019-2030, ISSN 0273-2289, tables 1, 2.
International Search Report for PCT/JP2018/020443 (PCT/ISA/210) dated Sep. 4, 2018.
Kokufuta et al., "Flocculation of Aspergillus terreus with Polyelectrolyte Complex and Production of Itaconic Acid with the Flocculated Mycelia", J. Ferment. Technol., 1988, vol. 66, No. 4, pp. 433-439, ISSN 0385-6380, fig. 1-5.
Kulkarni et al., "Improved Adsorption of Aspergillus niger 589 Spores on High-Density Polyethylene for Progesterone Biotransformation", Journal of Fermentation and Bioengineering, 1998, vol. 86, No. 5, pp. 510-512, ISSN 0922-338X, fig. 2, table 1.
Yamauchi, "Bioreactors using Immobilized Mold", Journal of the Brewing Society of Japan, 1992, vol. 87, No. 2, pp. 101-106, ISSN 2186-4012, table 1.
Zhang et al., "Metabolic engineering of Rhizopus oryzae: Effects of overexpressing pyc and pepc genes on fumaric acid biosynthesis from glucose", Metab. Eng ., 2012, vol. 14, pp. 512-520, ISSN 1096-7176, table 3.
Zhaoxin et al., "Effect of Carrier Ionic Properties on Cellulase Productivity by Immobilized Filamentous Trichoderma reesei", J. Chem. Tech. Biotechnol., 1994, vol. 60, pp. 183-187, ISSN 0268-2575, entire text.
Zlochevskaya, "Effect of polyethylenimine on some fungi, Vestnik Moskovskogo Universiteta, Seriya 6: Biologiya", Pochvovedenie, 1975, vol. 30, No. 3, pp. 69-73, ISSN 0579-9422, tables 1, 2.

* cited by examiner

*Primary Examiner* — Delia M Ramirez
(74) *Attorney, Agent, or Firm* — Birch, Stewart, Kolasch & Birch, LLP

(57) ABSTRACT

Provided is a method for producing a high-density filamentous fungal pellet.
A method for producing a filamentous fungal pellet, comprising a step of germinating spores of a filamentous fungus in a culture medium containing a cationic polymer.

12 Claims, No Drawings

PRODUCTION METHOD OF FILAMENTOUS FUNGUS PELLET

FIELD OF THE INVENTION

The present invention relates to a method for producing a filamentous fungal pellet.

BACKGROUND OF THE INVENTION

Filamentous fungi are useful microorganisms which are essential in industry for microbiologically producing useful substances such as organic acids and enzymes. Morphological forms of filamentous fungi cultured in liquids vary, for example, a fibrous form, a clumpy form, or a pelleted form, depending on, inoculation amounts of spores, pH in culture media, flow conditions, and the like. Filamentous fungal pellets are advantageous, for example, in that they are easily separated from a medium after fermentation (e.g., refer to Patent Literature 1).

Non Patent Literature 1 reports that filamentous fungal pellets are formed by addition of a specific nonionic surfactant to the culture medium. Further, Non Patent Literature 2 reports that mycelial aggregates of *Aspergillus niger* have been formed.

Patent Literature 1: JP H06-253871 A

Non Patent Literature 1: Journal of Industrial Microbiology, 4, p. 155-161 (1989)

Non Patent Literature 2: The 48th Meeting of the Society of Chemical Engineers of Japan, poster session LQ268

SUMMARY OF THE INVENTION

The present invention is to provide a method for producing a filamentous fungal pellet comprising a step of germinating spores of a filamentous fungus in a culture medium containing a cationic polymer, and a filamentous fungal pellet having a high mycelial density.

DETAILED DESCRIPTION OF THE INVENTION

The present invention relates to a provision of a method for producing a high-density filamentous fungal pellet.

As the result of studies on pelletizing a filamentous fungus, the present inventor found that a filamentous fungal pellet having a high mycelial density can be obtained by germinating filamentous fungal spores in a culture medium containing a cationic polymer, thereby causing the filamentous fungus to form a pellet.

According to the present invention, a high-density filamentous fungal pellet can be obtained.

The method for producing the filamentous fungal pellet of the present invention comprises a step of germinating spores of a filamentous fungus in a culture medium containing a cationic polymer, thereby causing the filamentous fungus to form a pellet.

(Filamentous Fungus)

Examples of the filamentous fungus used in the present invention include microorganisms belonging to the genus *Rhizopus*, the genus *Trichoderma*, the genus *Aspergillus*, and the genus *Mucor*.

Examples of the microorganism belonging to the genus *Rhizopus* include *Rhizopus delemar, Rhizopus oryzae, Rhizopus arrhizus, Rhizopus chinensis, Rhizopus nigricans, Rhizopus tonkinensis,* and *Rhizopus tritici.*

Examples of the microorganism belonging to the genus *Trichoderma* include *Trichoderma atroviride, Trichoderma harzianum, Trichoderma koningii, Trichoderma ressei,* and *Trichoderma viride.*

Examples of the microorganism belonging to the genus *Aspergillus* include *Aspergillus oryzae, Aspergillus niger,* and *Aspergillus terreus.*

Examples of the microorganism belonging to the genus *Mucor* include *Mucor mandshuricus.*

These filamentous fungi may be used singly, or in combination of two or more kinds thereof.

Of these, the microorganism belonging to the genus *Rhizopus* or the microorganism belonging to the genus *Trichoderma* is preferable, and *Rhizopus delemar* or *Rhizopus oryzae* is more preferable, from the standpoints of productivity of a useful substance and handleability. The useful substance in the present specification will be described later.

(Preparation of Filamentous Fungal Spores and Spore Suspension)

Spores of the filamentous fungus can be prepared as a spore suspension by inoculating spores of the filamentous fungus in a medium such as a potato dextrose agar medium (PDA medium) to perform static culturing and suspending the resulting culture in a liquid. The spore suspension can be appropriately diluted to adjust the number of spores to the desired number.

As conditions of the static culturing for preparing the spore suspension, the culture temperature is preferably 10° C. or higher, more preferably 25° C. or higher, and preferably 40° C. or lower, more preferably 30° C. or lower, from the standpoint of the propagation of spores. The culture period is preferably not less than 7 days and not more than 10 days.

The number of spores in the spore suspension can be measured by using a cell counter described later.

(Step of Spore Germination and Pelletization)

When the spore suspension is inoculated and cultured in a culture medium, the spore s are germinated and grown to a mycelium, resulting in formation of a pellet.

The term "pellet" described in the present specification refers to a mycelial mass of spontaneously formed by a mycelium due to liquid culturing, having an approximate size of from several hundreds of μm to several mm.

The number of the filamentous fungal spores to be inoculated in the culture medium is preferably $1 \times 10^1$ spores/mL of culture medium or more, more preferably $1 \times 10^2$ spores/mL of culture medium or more, from the standpoint of obtaining excellent growth of the filamentous fungal pellet. Further, from the similar standpoint to the above, the number of the filamentous fungal spores is preferably $1 \times 10^8$ spores/mL of culture medium or less, more preferably $1 \times 10^4$ spores/mL of culture medium or less.

The culture medium may be any of a synthetic medium, a natural medium, or a semisynthetic medium in which a natural component is added to a synthetic medium, as long as the medium is a liquid culture medium that can grow the filamentous fungus. For example, a potato dextrose medium (PDB medium), a Luria-Bertani medium (LB medium), a Nutrient Broth (NB medium), or a Sabouraud medium (SB medium) can be used.

The culture medium can include, for example, a carbon source, a nitrogen source, an inorganic salt, and other necessary nutrient sources.

As the carbon source, a saccharide can be mentioned. Examples of the saccharide include a monosaccharide such as glucose, fructose, and xylose and a disaccharide such as sucrose, lactose, and maltose. The saccharide may be an anhydrate or a hydrate. These may be used singly, or in combination of two or more kinds thereof. Of these, glucose is preferable from the standpoint of productivity. The initial concentration of the carbon source in the culture medium is preferably not less than 0.1% (w/v) and not more than 30% (w/v).

Examples of the nitrogen source include a nitrogen-containing compound such as urea, ammonium sulfate, ammonium nitrate, potassium nitrate, and sodium nitrate. The initial concentration of the nitrogen source in the culture medium is preferably not less than 0.1% (w/v) and not more than 1% (w/v).

Examples of the inorganic salt include a sulfate, a magnesium salt, and a zinc salt.

Examples of the sulfate include magnesium sulfate, zinc sulfate, potassium sulfate, and sodium sulfate. The initial concentration of the sulfate in the culture medium is preferably not less than 0.1% (w/v) and not more than 1% (w/v).

Examples of the magnesium salt include magnesium sulfate, magnesium nitrate, and magnesium chloride. The initial concentration of the magnesium salt in the culture medium is preferably not less than 0.0001% (w/v) and not more than 0.5% (w/v).

Examples of the zinc salt include zinc sulfate, zinc nitrate, and zinc chloride. The initial concentration of the zinc salt in the culture medium is preferably not less than 0.0001% (w/v) and not more than 0.5% (w/v).

(Cationic Polymer)

In the present invention, germination of spores and pelletization are performed in a culture medium containing a cationic polymer.

The term "cationic polymer" used in the present invention refers to a polymer that is positively charged upon mixing with water. Specific examples of the cationic polymer preferably include a polymer obtained from a monomer having a cationic group or a monomer having an amino group cationic in water, and a copolymer or condensation polymer obtained from these monomers and other monomers.

Examples of the cationic group include a quaternary amino group and a hydrazino group, and examples of the amino group cationic in water include a primary amino group, a secondary amino group, and a tertiary amino group.

A charge density of the cationic polymer is preferably 0.1 meq/g or more, more preferably 1 meq/g or more, still more preferably 2 meq/g or more, still more preferably 10 meq/g or more, from the standpoint of increasing a density of pellets. Further, from the similar standpoint to the above, a charge density of the cationic polymer is preferably 100 meq/g or less, more preferably 50 meq/g or less, still preferably 30 meq/g or less.

A charge density of the cationic polymer is preferably from 0.1 meq/g to 100 meq/g, more preferably from 1 meq/g to 50 meq/g, still more preferably from 2 meq/g to 30 meq/g, still more preferably from 10 meq/g to 30 meq/g.

The term "cationic charge density" described herein refers to a ratio between the number of positive charges on a polymer and the molecular weight of the polymer (excluding the weight of counterions of cationic groups). The number of positively charged sites in a given polymer chain can be obtained by multiplying the cationic charge density by the polymer molecular weight. The cationic charge density is further defined as a milliequivalent (meq/g) of positive charges (cationic nitrogen atoms) per gram of the polymer.

A value of the cationic charge density can be obtained, for example, according to the following Formula (1).

Cationic charge density (meq/g)=1/(molecular weight of unit containing one cationic nitrogen atom in the cationic polymer)×1000     (1)

A weight-average molecular weight (hereinafter, also simply ref erred to as "molecular weight") of the cationic polymer is preferably 1,000 or more, more preferably 1,600 or more, and preferably 1,000,000 or less, more preferably 500,000 or less, still more preferably 300,000 or less, still more preferably 200,000 or less, from the standpoint of obtaining excellent growth of the filamentous fungal pellet. The molecular weight of the cationic polymer is preferably from 1,000 to 1,000,000, more preferably from 1,000 to 500,000, still more preferably from 1,000 to 300,000, still more preferably from 1,600 to 200,000.

Further, the weight-average molecular weight of the cationic polymer is preferably 1,000 or more, more preferably 2,000 or more, still more preferably 5,000 or more, still more preferably 100,000 or more, and preferably 500,000 or less, from the standpoint of operability in culturing.

Note that the average molecular weight can be measured by a publicly known measurement method such as gel permeation chromatography (GPC) without limitation to a measurement apparatus. However, examples of the measurement apparatus include HLC-8220 series manufactured by Tosoh Corp.

The cationic polymer is preferably a water-soluble polymer. The term "water-soluble polymer" described herein refers to a polymer having a solubility in water of more than 10 g as measured by dissolving the polymer dried at 105° C. for 2 hours in 100 g of water at 25° C. The solubility of the cationic polymer in 100 g of water is preferably 20 g or more, more preferably 100 g or more.

Examples of the cationic polymer include a polymer containing a primary amine, a polymer containing a secondary amine, a polymer containing a tertiary amine, and a polymer containing a quaternary amine. Examples of the polymer containing a primary amine include poly-allylamine, an allylamine salt polymer, and an allylamine amide salt polymer. Examples of the polymer containing a secondary amine include poly-diallylamine, a diallylamine salt polymer, and a diallylamine salt/acrylamide copolymer. Examples of the polymer containing a tertiary amine include an alkyldiallylamine salt polymer and an alkyldiallylamine amide salt polymer. Examples of the polymer containing a quaternary amine include a diallyldialkyl ammonium salt polymer, a diallyldialkyl ammonium ethyl sulfate polymer, and a diallyldialkyl ammonium salt/acrylamide copolymer. Further, in addition to the above polymers, polyethylenimine, methyl glycol chitosan, an amine-epichlorohydrin copolymer, a cationized polyvinyl alcohol, cationized cellulose, cationized starch, cationized guar gum, and a dicyandiamide-based polymer can be mentioned. Examples of the above alkyl group include a methyl group, an ethyl group, and a propyl group. Further, examples of the above salt include a sulfate, a hydrochloride, and an acetate.

Examples of the allylamine salt polymer include an allylamine hydrochloride polymer. Examples of the allylamine amide salt polymer include an allylamine amide sulfate polymer. Examples of the diallylamine salt polymer include a diallylamine hydrochloride polymer. Examples of the alkyldiallylamine salt polymer include a methyldiallylamine hydrochloride polymer and a methyldiallylamine acetate polymer. Examples of the alkyldiallylamine amide salt polymer include methyldiallylamine amide sulfate polymer. Examples of the diallyldialkyl ammonium salt polymer include poly-diallyldimethyl ammonium chloride, poly-diallylmethylethyl ammonium chloride, poly-acrylic acid-codiallyldimethyl ammonium chloride, poly-acrylamide-co-diallyldimethyl ammonium chloride, poly-acrylamide-co-acrylic acid-co-diallyldimethyl ammonium chloride, poly-diallyldimethyl ammonium ethyl sulfate, and poly-diallylmethylethyl ammonium ethyl sulfate.

Examples of the diallyldialkyl ammonium ethyl sulfate polymer include diallylmethylethyl ammonium ethyl sulfate. Further, poly-2-(methacryloyloxy)ethyltrimethyl ammonium chloride can be mentioned.

The cationic polymers may be used singly, or in combination of two or more kinds thereof.

Of these, from the standpoint of increasing the density of pellets, polyethylenimine, poly-allylamine, an allylamine salt polymer, a diallyldialkyl ammonium salt polymer, a diallyldialkyl ammonium ethyl sulfate polymer, methyl glycol chitosan, and a cationized polyvinyl alcohol are preferable; polyethylenimine, poly-allylamine, an allylamine salt polymer, and a diallyldialkyl ammonium salt polymer are more preferable; and polyethylenimine, poly-allylamine, a diallyldialkyl ammonium salt polymer are still more preferable.

The content of the cationic polymer in the culture medium is preferably 0.0001% (w/v) or more, more preferably 0.001% (w/v) or more, still more preferably 0.0015% (w/v) or more, from the standpoint of increasing the density of pellets. Further, from the similar standpoint to the above, the content of the cationic polymer in the culture medium is preferably 2% (w/v) or less, more preferably 1% (w/v) or less, still more preferably 0.5% (w/v) or less. The content of the cationic polymer in the culture medium is preferably from 0.0001 to 2% (w/v), more preferably from 0.001% to 1% (w/v), still more preferably from 0.0015 to 0.5% (w/v).

(Culture Method During Spore Germination and Pelletization)

Culturing may be performed by a normal procedure. Culturing is normally performed under an aerobic condition.

The culture temperature is preferably 20° C. or higher, more preferably 25° C. or higher, and preferably 40° C. or lower, more preferably 30° C. or lower.

The initial pH of the medium is preferably 2 or higher, more preferably 3 or higher, and preferably 7 or lower, more preferably 5 or lower, from the standpoint of obtaining excellent growth of the fungal cells.

The culture period is preferably 30 minutes or more, more preferably 0.5 days or more, and preferably 7 days or less, more preferably 6 days or less, still more preferably 5 days or less, after the spore s of the filamentous fungus are inoculated in the culture medium.

As a culture vessel used for culturing, a conventionally known culture vessel can be appropriately employed. Examples of the culture vessel include a flask, a stirred tank reactor, a bubble-column reactor, and a fluidized-bed reactor. The agitation condition is preferably 80 r/min or more, more preferably 100 r/min or more, and preferably 250 r/min or less, more preferably 200 r/min or less.

The pellet having a desired size and appearance can be formed by changing, for example, the culture temperature, the culture period, and the agitation condition.

A volume average particle diameter of the filamentous fungal pellet is preferably 150 μm or more, more preferably 250 μm or more, and preferably 3000 μm or less, more preferably 1500 μm or less, from the standpoints of high productivity of a useful substance and separability in using a catalyst repeatedly.

Note that the volume average particle diameter can be measured by performing image analysis with microscopic observation described later.

(Pellet Propagation Step)

In the present invention, a step of further culturing and propagating the filamentous fungal pellet may be performed from the standpoint of improving productivity of a useful substance.

No particular limitation is imposed on the culture medium used for propagating the filamentous fungal pellet. However, the culture medium to be use is preferably different from the one used in the step of germinating the spores of the filamentous fungus. Examples of such a culture medium include a normally used inorganic culture medium containing glucose. Specific examples thereof include a medium containing glucose in an amount of not less than 7.5 and not more than 30% (w/v), ammonium sulfate in an amount of not less than 0.05 and not more than 2% (w/v), potassium dihydrogen phosphate in an amount of not less than 0.03 and not more than 0.6% (w/v), magnesium sulfate in an amount of not less than 0.01 and not more than 0.1% (w/v), and zinc sulfate in an amount of not less than 0.005 and not more than 0.05% (w/v). The salts described above may be hydrates.

As the culture condition, the culture temperature is preferably 20° C. or higher, more preferably 25° C. or higher, and preferably 40° C. or lower, more preferably 30° C. or lower.

Further, the pH of the medium is preferably 2 or higher, more preferably 3 or higher, and preferably 7 or lower, more preferably 5 or lower, from the standpoints of growth of the fungal cells and productivity of a useful substance. The pH of the culture medium can be controlled by using a base such as calcium hydroxide, sodium hydroxide, calcium carbonate, and ammonia and an acid such as sulfuric acid and hydrochloric acid.

The culture period is preferably 30 minutes or more, more preferably 6 hours or more, still more preferably 0.5 days or more, and preferably 3 days or less, more preferably 2 days or less, still more preferably 1 day or less.

Further, as a culture vessel used for culturing, a conventionally known culture vessel can be appropriately employed. Specific examples thereof include a flask, a stirred tank reactor, a bubble-column reactor, and a fluidized-bed reactor.

After culturing, the filamentous fungal pellet is taken out from the culture vessel together with the culture medium, and the filamentous fungal pellet can be separated and collected by a simple operation such as filtration and centrifugal separation. The filamentous fungal pellet can be left in the culture vessel and used for producing a substance in the same culture vessel.

The filamentous fungal pellet obtained in this manner has a high mycelial density. Thus, the filamentous fungal pellet is useful for improving fermentative productivity of a useful substance.

The density of the filamentous fungal pellet is 0.04 g-dry cell/cm$^3$ or more, more preferably 0.1 g-dry cell/cm$^3$ or more, and 0.5 g-dry cell/cm$^3$ or less, more preferably 0.3 g-dry cell/cm$^3$ or less, still more preferably 0.25 g-dry cell/cm$^3$ or less, from the standpoint of productivity of a useful substance. The density can be obtained by a method described in Example below.

A useful substance in the present specification is a compound produced from a carbon source in the process of culturing the filamentous fungus. Examples of such a compound include at least one selected from the group consisting of an organic acid, an enzyme, a fat or oil, or an alcohol. A preferably useful substance that can be produced by using the filamentous fungal pellet of the present invention is an organic acid, ethanol, or an enzyme. Examples of the organic acid include fumaric acid, lactic acid, itaconic acid, malic acid, and pyruvic acid. Of these, at least one selected from the group consisting of fumaric acid, pyruvic acid, lactic acid, and malic acid is preferable; fumaric acid or lactic acid is more preferable; and fumaric acid is still more preferable. Examples of the enzyme include protease, oxygenase, amylase, cellulase, and isomerase.

(Production of Useful Substance Using Filamentous Fungal Pellet)

The culture medium used in producing the useful substance normally contains a carbon source. The culture medium can contain, for example, a nitrogen source, an inorganic salt, and other nutrient sources such as a phosphorus source and a vitamin, in addition to the carbon source. The carbon source can be used alone provided that the carbon source to be used contains the above nutrient sources at concentrations appropriate for culturing. As the carbon source, the nitrogen source, and the inorganic salt, compounds described in the above paragraph [0014] can be mentioned.

In the culture medium used in producing the useful substance, as the carbon source, a carbohydrate solution containing a saccharide can be used. Examples of the carbohydrate solution include a carbohydrate solution obtained from starch, molasses, blackstrap molasses, and a carbohydrate solution obtained from lignocellulose-based biomass. These may be used singly, or in combination of two or more kinds thereof. The term "lignocellulose-based biomass" in the present specification refers to biomass containing cellulose, hemicellulose, and lignin as main components. Specific examples of the lignocellulose-based biomass include a rice straw, a chaff, a wheat straw, a bagasse, a palm shell, a corn cob, a weed, a wood, and pulp or paper produced therefrom. Further, examples of the starch include extract of a cereal such as corn and a bean such as soybean. Examples of the molasses include one derived from sugarcane, sugar beet, or the like.

The initial concentration of the carbon source in the culture medium is preferably it (w/v) or more, more preferably 2% (w/v) or more, still more preferably 3% (w/v) or more, and preferably 40% (w/v) or less, more preferably 30% (w/v) or less, still more preferably 20% (w/v) or less, from the standpoint of productivity. Further, the initial concentration of the carbon source in the culture medium is preferably from 1 to 40 (w/v) %, more preferably from 2 to 30 (w/v) %, still more preferably from 3 to 20 (w/v) %.

Further, the initial concentration of the nitrogen source in the culture medium is preferably 0.001% (w/v) or more, more preferably 0.002% (w/v) or more, still more preferably 0.004% (w/v) or more, and preferably 0.5% (w/v) or less, more preferably 0.3% (w/v) or less, still more preferably 0.1% (w/v) or less, from the standpoint of productivity.

The initial concentration of the sulfate in the culture medium is preferably 0.001% (w/v) or more, more preferably 0.005% (w/v) or more, still more preferably 0.01% (w/v) or more, and preferably 0.1% (w/v) or less, more preferably 0.08% (w/v) or less, still more preferably 0.04% (w/v) or less, from the standpoint of productivity.

The initial concentration of the magnesium salt in the culture medium is preferably 0.001% (w/v) or more, more preferably 0.002% (w/v) or more, still more preferably 0.003% (w/v) or more, and preferably 0.5% (w/v) or less, more preferably 0.2% (w/v) or less, still more preferably 0.1% (w/v) or less, from the standpoint of productivity.

The initial concentration of the zinc salt in the culture medium is preferably 0.00001% (w/v) or more, more preferably 0.00003% (w/v) or more, still more preferably 0.00005% (w/v) or more, and preferably 0.1% (w/v) or less, more preferably 0.05% (w/v) or less, still more preferably 0.01% (w/v) or less, from the standpoint of productivity.

The culture temperature in producing the useful substance is preferably 20° C. or higher, more preferably 30° C. or higher, and preferably 40° C. or lower, more preferably 37° C. or lower.

The pH of the culture medium is preferably 2 or higher, more preferably 3 or higher, and preferably 7 or lower, more preferably 5 or lower, from the standpoints of growth of the fungal cells and productivity of a useful substance. The pH can be controlled by using a base such as calcium hydroxide, sodium hydroxide, calcium carbonate, and ammonia and an acid such as sulfuric acid and hydrochloric acid.

As gas used for culturing, air or an oxygen-enriched gas can be selected. The aeration condition is preferably 0.1 vvm or more, more preferably 0.2 vvm or more, and preferably 2 vvm or less, more preferably 1 vvm or less.

Further, as a culture vessel used for culturing, a conventionally known culture vessel can be appropriately employed. A stirred tank reactor, a bubble-column reactor, and a fluidized-bed reactor are preferably used from the standpoint of high productivity of fumaric acid.

Culturing may be any of a batch culture, a semi-batch culture, and a continuous culture. For example, when the culturing is a semi-batch culture, the fungal cells can be separated from the fermentation liquid, and a medium can be added to the fungal cells thus separated and collected to further perform fermentation. Further, when the culturing is the continuous culture, a method in which a certain amount of a medium is supplied to the fermentation vessel at a certain rate while the same amount of the fermentation liquid is taken out from the fermentation vessel can be employed. In such a case, the liquid level in the fermentation vessel can be controlled so as to be constant by using, for example, a liquid level sensor.

Further, only the carbon source can be supplied during fermentation, and, in such a case, supply of the carbon source may be controlled on the basis of a flow rate or a glucose concentration.

After culturing, the fungal cells may be separated from the fermentation liquid by solid-liquid separation using a filter in the fermentation vessel. Alternatively, the fungal cells and the fermentation liquid may be temporarily taken out from the vessel and subjected to solid-liquid separation by means of, for example, a liquid cyclone or filtration, and then only the fungal cells may be returned to the fermentation vessel.

(Collection of Useful Substance)

The fermentation liquid obtained after separation is, directly or after being concentrated, subjected to a crystallization method, an ion exchange method, a solvent extraction method, a method in which a precipitate obtained as an alkaline earth metal salt is acid-hydrolyzed, or the like, thereby making it possible to separate and collect a product from the fermentation liquid.

Regarding the embodiment described above, the present invention further discloses the following production methods.

<1> A method for producing a filamentous fungal pellet, comprising a step of germinating spores of a filamentous fungus in a culture medium containing a cationic polymer.

<2> The method for producing the filamentous fungal pellet as described in <1>, in which the filamentous fungus is preferably one or more selected from the group consisting of microorganisms belonging to the genus *Rhizopus*, the genus *Trichoderma*, the genus *Aspergillus*, and the genus *Mucor*; more preferably one or more selected from the group consisting of *Rhizopus delemar, Rhizopus oryzae, Rhizopus arrhizus, Rhizopus chinensis, Rhizopus nigricans, Rhizopus tonkinensis, Rhizopus tritici, Trichoderma atroviride, Trichoderma harzianum, Trichoderma koningii, Trichoderma ressei, Trichoderma viride, Aspergillus oryzae, Aspergillus niger, Aspergillus terreus,* or *Mucor mandshuricus*.

<3> The method for producing the filamentous fungal pellet as described in <1>, in which the filamentous fungus is preferably the microorganism belonging to the genus *Rhizopus* or the genus *Trichoderma*; more preferably *Rhizopus delemar, Rhizopus oryzae,* and *Trichoderma ressei*.

<4> The method for producing the filamentous fungal pellet as described in any one of <1> to <3>, in which the spores of the filamentous fungus are inoculated in a culture medium containing a cationic polymer with the number of spores of preferably $1\times10^1$ spores/mL of culture medium or more, more preferably $1\times10^2$ spores/mL of culture medium or more, and preferably $1\times10^8$ spores/mL of culture medium or less, more preferably $1\times10^4$ spores/mL of culture medium or less to germinate the spores.

<5> The method for producing the filamentous fungal pellet as described in any one of <1> to <4>, in which the culture medium preferably contains a carbon source, a nitrogen source, and an inorganic salt.

<6> The method for producing the filamentous fungal pellet as described in <5>, in which, in the culture medium, an initial concentration of the nitrogen source is preferably not less than 0.1% (w/v) and not more than 1% (w/v), an initial concentration of a sulfate is preferably not less than 0.1% (w/v) and not more than 1% (w/v), an initial concentration of a magnesium salt is preferably not less than 0.0001% (w/v) and not more than 0.5% (w/v), and an initial concentration of a zinc salt is preferably not less than 0.0001% (w/v) and not more than 0.5% (w/v).

<7> The method for producing the filamentous fungal pellet as described in any one of <1> to <6>, in which a content of the cationic polymer in the culture medium is preferably 0.0001% (w/v) or more, more preferably 0.001% (w/v) or more, still more preferably 0.0015% (w/v) or more; preferably 2% (w/v) or less, more preferably 1% (w/v) or less, still more preferably 0.5% (w/v) or less; and preferably from 0.0001 to 2% (w/v), more preferably from 0.001 to 1% (w/v), still more preferably from 0.0015 to 0.5% (w/v).

<8> The method for producing the filamentous fungal pellet as described in any one of <1> to <7>, in which a charge density of the cationic polymer is preferably 0.1 meq/g or more, more preferably 1 meq/g or more, still more preferably 2 meq/g or more, still more preferably 10 meq/g or more; preferably 100 meq/g or less, more preferably 50 meq/g or less, still preferably 30 meq/g or less; and preferably from 0.1 meq/g to 100 meq/g, more preferably from 1 meq/g to 50 meq/g, still more preferably from 2 meq/g to 30 meq/g, still more preferably from 10 meq/g to 30 meq/g.

<9> The method for producing the filamentous fungal pellet as described in any one of <1> to <8>, in which a weight-average molecular weight of the cationic polymer is preferably 1,000 or more, more preferably 1,600 or more; preferably 1,000,000 or less, more preferably 500,000 or less, still more preferably 300,000 or less, still more preferably 200,000 or less; and preferably from 1,000 to 1,000,000, more preferably from 1,000 to 500,000, still more preferably from 1,000 to 300,000, still more preferably from 1,600 to 200,000.

<10> The method for producing the filamentous fungal pellet as described in any one of <1> to <8>, in which a weight-average molecular weight of the cationic polymer is preferably 1,000 or more, more preferably 2,000 or more, still more preferably 5,000 or more, still more preferably 100,000 or more; preferably 500,000 or less; and preferably from 1,000 to 500,000, more preferably from 2,000 to 500,000, still more preferably from 5,000 to 500,000, still more preferably from 100,000 to 500,000.

<11> The method for producing the filamentous fungal pellet as described in any one of <1> to <10>, in which the cationic polymer is preferably a water-soluble cationic polymer.

<12> The method for producing the filamentous fungal pellet as described in any one of <1> to <11>, in which the cationic polymer is preferably one or more selected from the group consisting of a poly-diallyldialkyl ammonium salt or a copolymer thereof, polyethylenimine, poly-allylamine or a salt thereof, methyl glycol chitosan, an amine-epichlorohydrin copolymer, a cationized polyvinyl alcohol, cationized cellulose, cationized starch, cationized guar gum, a dicyandiamide-based polymer, and poly-2-(methacryloyloxy)ethyltrimethyl ammonium chloride; and more preferably one or more selected from the group consisting of poly-allylamine or a salt thereof, methyl glycol chitosan, a poly-diallyldialkyl ammonium salt or a copolymer thereof, polyethylenimine, and a cationized polyvinyl alcohol.

<13> The method for producing the filamentous fungal pellet as described in <12>, in which the poly-diallyldialkyl ammonium salt or the copolymer thereof is preferably one or more selected from the group consisting of poly-diallyldimethyl ammonium chloride, poly-diallylmethylethyl ammonium chloride, poly-acrylic acid-co-diallyldimethyl ammonium chloride, poly-acrylamide-co-diallyldimethyl ammonium chloride, poly-acrylamide-co-acrylic acid-co-diallyldimethyl ammonium chloride, poly-diallyldimethyl ammonium ethyl sulfate, and poly-diallylmethylethyl ammonium ethyl sulfate.

<14> The method for producing the filamentous fungal pellet as described in any one of <1> to <13>, in which a culture temperature is preferably 20° C. or higher, more preferably 25° C. or higher; and preferably 40° C. or lower, more preferably 30° C. or lower.

<15> The method for producing the filamentous fungal pellet as described in any one of <1> to <14>, in which an initial pH of the culture medium containing the cationic polymer is preferably 2 or higher, more preferably 3 or higher; and preferably 7 or lower, more preferably 5 or lower.

<16> The method for producing the filamentous fungal pellet as described in any one of <1> to <15>, in which a culture period is preferably 30 minutes or more, more preferably 0.5 days or more; and preferably 7 days or less, more preferably 6 days or less, still more preferably 5 days or less.

<17> The method for producing the filamentous fungal pellet as described in any one of <1> to <16>, in which a volume average particle diameter of the filamentous fungal pellet is preferably 150 μm or more, more preferably 250 μm or more; and preferably 3000 μm or less, more preferably 1500 μm or less.

<18> The method for producing the filamentous fungal pellet as described in any one of <1> to <17>, further comprising a step of propagating the filamentous fungal pellet in a culture medium different from the culture medium in the step of germinating the spores of the filamentous fungus.

<19> The method for producing the filamentous fungal pellet as described in <18>, in which the culture medium used for propagating the filamentous fungal pellet preferably contains glucose in an amount of 7.5 to 30% (w/v), ammonium sulfate in an amount of 0.05 to 2% (w/v), potassium dihydrogen phosphate in an amount of 0.03 to 0.6% (w/v), magnesium sulfate heptahydrate in an amount of 0.01 to 0.1% (w/v), and zinc sulfate heptahydrate in an amount of 0.005 to 0.05% (w/v).

<20> The method for producing the filamentous fungal pellet as described in <18> or <19>, in which the culture temperature in the step of propagating the filamentous fungal pellet is preferably 20° C. or higher, more preferably 25° C. or higher; and preferably 40° C. or lower, more preferably 30° C. or lower.

<21> The method for producing the filamentous fungal pellet as described in any one of <18> to <20>, in which a pH of the culture medium in the step of propagating the filamentous fungal pellet is preferably 2 or higher, more preferably 3 or higher; and preferably 7 or lower, more preferably 5 or lower.

<22> The method for producing the filamentous fungal pellet as described in any one of <18> to <21>, in which a culture period in the step of propagating the filamentous fungal pellet is preferably 30 minutes or more, more preferably 6 hours or more, still more preferably 0.5 days or more; and preferably 3 days or less, more preferably 2 days or less, still more preferably 1 day or less.

<23> The method for producing the filamentous fungal pellet as described in any one of <1> to <22>, in which a density of the filamentous fungal pellet is preferably 0.04 g-dry cell/cm$^3$ or more, more preferably 0.1 g-dry cell/cm$^3$ or more; and preferably 0.5 g-dry cell/cm$^3$ or less, more preferably 0.3 g-dry cell/cm$^3$ or less, still more preferably 0.25 g-dry cell/cm$^3$ or less.

<24> A method for producing at least one selected from the group consisting of an organic acid and ethanol, comprising using the filamentous fungal pellet obtained by the production method as described in any one of <1> to <23> in a culture medium containing a carbon source.

<25> The method as described in <24>, in which the organic acid is preferably at least one selected from the group consisting of fumaric acid, lactic acid, itaconic acid, malic acid, or pyruvic acid; more preferably at least one selected from fumaric acid, pyruvic acid, lactic acid, or malic acid; still more preferably fumaric acid or lactic acid; and still more preferably fumaric acid.

<26> The method as described in <24> or <25>, in which an initial concentration of the carbon source in the culture medium is preferably 1% (w/v) or more, more preferably 2% (w/v) or more, still more preferably 3% (w/v) or more; and preferably 40% (w/v) or less, more preferably 30% (w/v) or less, still more preferably 20% (w/v) or less; and preferably from 1 to 40 (w/v) %, more preferably from 2 to 30 (w/v) %, still more preferably from 3 to 20 (w/v) %.

<27> The method as described in any one of <24> to <26>, in which the culture medium preferably contains a nitrogen source and an inorganic salt.

<28> The method as described in <27>, in which, in the culture medium, an initial concentration of the nitrogen source is preferably 0.001% (w/v) or more, more preferably 0.002% (w/v) or more, still more preferably 0.004% (w/v) or more; and preferably 0.5% (w/v) or less, more preferably 0.3% (w/v) or less, still more preferably 0.1% (w/v) or less; an initial concentration of a sulfate is preferably 0.001% (w/v) or more, more preferably 0.005% (w/v) or more, still more preferably 0.01% (w/v) or more; and preferably 0.1% (w/v) or less, more preferably 0.08% (w/v) or less, still more preferably 0.04% (w/v) or less; an initial concentration of a magnesium salt is preferably 0.001% (w/v) or more, more preferably 0.002% (w/v) or more, still more preferably 0.003% (w/v) or more; and preferably 0.5% (w/v) or less, more preferably 0.2% (w/v) or less, still more preferably 0.1% (w/v) or less; and an initial concentration of a zinc salt is preferably 0.00001% (w/v) or more, more preferably 0.00003% (w/v) or more, still more preferably 0.00005% (w/v) or more; and preferably 0.1% (w/v) or less, more preferably 0.05% (w/v) or less, still more preferably 0.01% (w/v) or less.

<29> The method as described in any one of <24> to <28>, in which a culture temperature when producing at least one selected from the group consisting of an organic acid and ethanol is preferably 20° C. or higher, more preferably 30° C. or higher; and preferably 40° C. or lower, more preferably 37° C. or lower.

<30> The method as described in any one of <24> to <29>, in which a pH of the culture medium is preferably 2 or higher, more preferably 3 or higher; and preferably 7 or lower, more preferably 5 or lower.

<31> A filamentous fungal pellet, having a density of preferably 0.04 g-dry cell/cm$^3$ or more, more preferably 0.1 g-dry cell/cm$^3$ or more; and preferably 0.5 g-dry cell/cm$^3$ or less, more preferably 0.3 g-dry cell/cm$^3$ or less, still more preferably 0.25 g-dry cell/cm$^3$ or less.

<32> The filamentous fungal pellet as described in <31>, having a volume average particle diameter of preferably 150 µm or more, more preferably 250 µm or more; and preferably 3000 µm or less, more preferably 1500 µm or less.

EXAMPLES

[Cationic Polymer]

The following polymers were used in Examples 1 to 16.

Polyethylenimine (PEI, molecular weight 10,000, charge density 23.2 meq/g, manufactured by Alfa Asesar)

Poly-allylamine (PAA-01, molecular weight 1,600, charge density 17.5 meq/g, manufactured by Nittobo Medical Co., Ltd.)

Poly-allylamine (PAA-05, molecular weight 5,000, charge density 17.5 meq/g, manufactured by Nittobo Medical Co., Ltd.)

Poly-allylamine (PAA-15c, molecular weight 15,000, charge density 17.5 meq/g, manufactured by Nittobo Medical Co., Ltd.)

Poly-allylamine (PAA-25, molecular weight 25,000, charge density 17.5 meq/g, manufactured by Nittobo Medical Co., Ltd.)

Poly-allylamine hydrochloride (PAA-HCl-01, molecular weight 1,600, charge density 10.7 meq/g, manufactured by Nittobo Medical Co., Ltd.)

Poly-allylamine hydrochloride (PAA-HCl-05, molecular weight 5,000, charge density 10.7 meq/g, manufactured by Nittobo Medical Co., Ltd.)

Poly-allylamine hydrochloride (PAA-HCl-3L, molecular weight 30,000, charge density 10.7 meq/g, manufactured by Nittobo Medical Co., Ltd.)

Poly-allylamine hydrochloride (PAA-HCl-10L, molecular weight 150,000, charge density 10.7 meq/g, manufactured by Nittobo Medical Co., Ltd.)

Poly-diallyldimethyl ammonium chloride (PAS-H, molecular weight 200,000, charge density 6.19 meq/g, manufactured by Nittobo Medical Co., Ltd.)

Poly-diallylmethylethyl ammonium ethyl sulfate (PAS-24, molecular weight 37,000, charge density 3.32 meq/g, manufactured by Nittobo Medical Co., Ltd.)

Methyl glycol chitosan (MGch, molecular weight 150,080, charge density 2.67 meq/g, manufactured by Wako Pure Chemical Industries, Ltd.)

Poly-allylamine hydrochloride (PAH, molecular weight 120,000 to 200,000, charge density 10.7 meq/g, manufactured by Alfa Asesar)

Poly-allylamine (PAAm, molecular weight 15,000, charge density 17.5 meq/g, manufactured by Polysciences, Inc.)

Cationized polyvinyl alcohol (GOHSENX K-434, C-PVA, molecular weight 78,000 to 86,000, charge density 8.23 meq/g, manufactured by Nippon Synthetic Chemical Industry Co., Ltd.)

[Surfactant]

The following surfactant was used in Comparative examples 1 and 6.

(Nonionic Surfactant)

Sorbitan monolaurate: RHEODOL SP-L10, molecular weight 346.46, manufactured by Kao Corp.

[Polymer]

The following polymers were used in Comparative examples 3 and 4.

(Nonionic Polymer)

Polyvinyl alcohol (PVA, molecular weight 100,000, manufactured by Polysciences, Inc.)

(Anionic Polymer)

Sodium polyacrylate (SPA, molecular weight 2,821,200 to 3,761,600, manufactured by Wako Pure Chemical Industries, Ltd.)

Example 1

<Preparation of Filamentous Fungal Pellet>
[Preparation of Spore Suspension]

A fungal strain used was a filamentous fungus *R. delemar* JCM5557 obtained from National Institute of Technology and Evaluation (NITE). Fungal cells of the filamentous fungus were streaked and applied on a PDA medium (Difco Potato Dextrose Agar, manufactured by Becton, Dickinson and Company) prepared in a petri dish and statically cultured at 30° C. The fungal cells were regularly sub-cultured in this manner. When using the fungal cells, spores were collected from the petri dish and suspended into 40 mL of a solution for collecting spores (NaCl 0.85% and Tween80 0.05%). The collected spores were then diluted with a sterile solution for collecting spores (NaCl 0.85% and Tween80 0.05%) to adjust to $1 \times 10^7$ spores/mL and used as a spore suspension. The concentration of spores was measured with an automated cell counter (TC20™, manufactured by Bio-Rad Laboratories, Inc.).

[Germination and Pelletization of Filamentous Fungus]

To a 500 mL Erlenmeyer flask equipped with baffles in which 200 mL of a heat-sterilized PDB medium (Difco Potato Dextrose Broth, manufactured by Becton, Dickinson and Company) was placed, heat-sterilized polyethylenimine was added to provide 0.0015% (w/v). The spore suspension was inoculated in the PDB medium in an amount of $2 \times 10^3$ spores/mL and cultured for 3 days under shaking conditions of 27° C. and 170 r/min using a shaker (PRXYg-98R, manufactured by Preci Co., Ltd.) to germinate the filamentous fungus, thereby obtaining the filamentous fungal pellet.

<Measurement of Density Per Filamentous Fungal Pellet>

After completing the culturing, 100 mL of the culture medium containing the fungal cells was sampled for measuring the weight. The filamentous fungal pellet was separated by filtration using a nylon membrane filter (an opening of 180 μm, manufactured by Millipore Corp.). Next, the filamentous fungal pellet thus separated was immersed into 200 mL of distilled water and stirred for 15 minutes under conditions of 170 r/min and 27° C. using a shaker (PRXYg-98R, manufactured by Preci Co., Ltd.), followed by separating by filtration using the aforementioned nylon membrane filter. This washing operation was repeated three times.

The filamentous fungal pellet after washing was filtered again with the nylon membrane filter and allowed to stand for 1 day in a dryer of 105° C. to obtain dried fungal cells. The weight of the dried fungal cells was measured to obtain a dry weight concentration of fungal cells [g-dry cell/L].

A pellet particle number concentration [number of pellets/L] was obtained by counting the number of pellets present per mL by visual observation after washing.

A pellet volume per pellet [cm³/pellet] was calculated by observing the filamentous fungal pellets after washing through image analysis (VHX-1000, manufactured by Keyence Corp.) and obtaining a volume average particle diameter of one hundred pellets.

A density per filamentous fungal pellet was calculated by the following Formula (1).

Filamentous fungal pellet density [g-dry cell/cm³]=
dry weight concentration of fungal cells [g-dry cell/L]/pellet particle number concentration [number of pellets/L]/volume per filamentous fungal pellet [cm³/pellet]     (1)

[Example 2] to [Example 12]

The filamentous fungal pellet was obtained by a similar manner to that in Example 1 except that a cationic polymer shown in Table 1 was used.

Example 13

The filamentous fungal pellet was obtained by a similar manner to that in Example 1 except that poly-allylamine hydrochloride (molecular weight 120,000 to 200,000, charge density 10.7, manufactured by Alfa Asesar) was used as a cationic polymer and the addition concentration was set to 0.5% (w/v).

[Example 14] and [Example 15]

The filamentous fungal pellet was obtained by a similar manner to that in Example 13 except that the addition concentration of the poly-allylamine hydrochloride was set to 0.1% (w/v) or 0.01% (w/v).

Example 16

<Preparation of Filamentous Fungal Pellet>
[Spore Collection and Preparation of Frozen Stock]

A fungal strain used was a filamentous fungus, *Trichoderma ressei*. Fungal cells of the filamentous fungus were steaked and applied on a PDA medium (Difco Potato Dextrose Agar, manufactured by Becton, Dickinson and Company) prepared in a petri dish and statically cultured at 30° C. for 7 day to thereby sufficiently form spores. After the static culturing, spores were collected from the petri dish and suspended into a solution for collecting spores (NaCl 0.9%, Tween80 0.03%). The concentration of spores was measured with an automated cell counter (TC20™, manufactured by Bio-Rad Laboratories, Inc.). After the spore suspension was prepared, the suspension and a glycerol aqueous solution (40 volt) were mixed with a volume ratio of 3:1, and the resulting mixture was stored at −80° C. in an ultra-low temperature freezer (manufactured by Sanyo Electric Co., Ltd,) to prepare a frozen stock.

[Germination and Pelletization of Filamentous Fungus]

To a 500 mL Erlenmeyer flask, 50 mL of a PDB medium and 0.0045% (w/v) of a cationized polyvinyl alcohol were placed. After the Erlenmeyer flask was heat-sterilized, the frozen spore suspension was thawed and then inoculated in the medium in an amount of $1 \times 10^4$ spores/mL. The spore suspension was cultured for 2 days under shaking conditions of 28° C. and 220 r/min using a shaker (PRXYg-98R, manufactured by Preci Co., Ltd.) to obtain the filamentous fungal pellet.

<Measurement of Density Per Filamentous Fungal Pellet>

After completing the culturing, 50 mL of the culture medium containing the fungal cells thus obtained was washed by a similar manner to that in Example 1 described above, and then a filamentous fungal pellet density [g-dry cell/cm$^3$] was calculated.

Comparative Example 1

<Preparation of Filamentous Fungal Pellet>
[Preparation of Spore Suspension]

The spore suspension was prepared by a similar manner to that in Example 1 described above.

[Pelletization of Filamentous Fungus]

To a 500 mL Erlenmeyer flask equipped with baffles, 200 mL of a PDB medium and 0.5% (w/v) of sorbitan monolaurate were placed. After the Erlenmeyer flask was heat-sterilized, the spore suspension was inoculated in the medium in an amount of $2 \times 10^3$ spores/mL and cultured for 3 days under shaking conditions of 27° C. and 170 r/min using a shaker (PRXYg-98R, manufactured by Preci Co., Ltd.) to obtain the filamentous fungal pellet.

<Measurement of Density Per Filamentous Fungal Pellet>

After completing the culturing, washing was performed by a similar manner to that in Example 1 described above, and then a filamentous fungal pellet density [g-dry cell/cm$^3$] was calculated.

Comparative Example 2

Culturing was performed by a similar manner to that in Comparative example 1 without using an additive.

Comparative Example 3

The filamentous fungal pellet was obtained by a similar manner to that in Comparative example 2 except that a polyvinyl alcohol (0.5% (w/v)) was used as an additive.

Comparative Example 4

The filamentous fungal pellet was obtained by a similar manner to that in Comparative example 3 except that sodium polyacrylate (0.5% (w/v)) was used as an additive.

Comparative Example 5

Culturing was performed by a similar manner to that in Example 16 without using an additive.

Results of Examples 1 to 16 and Comparative examples 1 to 5 are shown in Table 1 and Table 2.

TABLE 1

| | Types of additives | | Charge density [meq/g] | Molecular weight | Concentration of additive [%(w/v)] | Filamentous fungal pellet density [g-dry cell/cm$^3$] |
|---|---|---|---|---|---|---|
| Example 1 | Polyethylenimine | PEI | 23.2 | 10,000 | 0.0015 | 0.150 |
| Example 2 | Poly-allylamine | PAA-01 | 17.5 | 1,600 | 0.0015 | 0.124 |
| Example 3 | Poly-allylamine | PAA-05 | 17.5 | 5,000 | 0.0015 | 0.112 |
| Example 4 | Poly-allylamine | PAA-15c | 17.5 | 15,000 | 0.0015 | 0.105 |
| Example 5 | Poly-allylamine | PAA-25 | 17.5 | 25,000 | 0.0015 | 0.130 |
| Example 6 | Poly-allylamine hydrochloride | PAA-HCl-01 | 10.7 | 1,600 | 0.0015 | 0.089 |
| Example 7 | Poly-allylamine hydrochloride | PAA-HCl-05 | 10.7 | 5,000 | 0.0015 | 0.088 |
| Example 8 | Poly-allylamine hydrochloride | PAA-HCl-3L | 10.7 | 30,000 | 0.0015 | 0.097 |
| Example 9 | Poly-allylamine hydrochloride | PAA-HCl-10L | 10.7 | 150,000 | 0.0015 | 0.104 |
| Example 10 | Poly-diallyldimethyl ammonium chloride | PAS-H | 6.19 | 200,000 | 0.0015 | 0.140 |
| Example 11 | Poly-diallylmethylethyl ammonium ethyl sulfate | PAS-24 | 3.32 | 37,000 | 0.0015 | 0.071 |
| Example 12 | Methyl glycol chitosan | MGCh | 2.67 | 150,080 | 0.0015 | 0.046 |
| Example 13 | Poly-allylamine hydrochloride | PAH | 10.7 | 120,000~200,000 | 0.5000 | 0.261 |
| Example 14 | Poly-allylamine hydrochloride | PAH | 10.7 | 120,000~200,000 | 0.1000 | 0.195 |
| Example 15 | Poly-allylamine hydro chloride | PAH | 10.7 | 120,000~200,000 | 0.0100 | 0.067 |
| Comparative example 1 | Sorbitan monolaurate | SP-L10 | — | 346.46 | 0.5000 | 0.027 |
| Comparative example 2 | No additive | — | — | — | — | Aggregation of pellets |
| Comparative example 3 | Polyvinyl alcohol | PRVA | — | 100,000 | 0.5000 | Aggregation of pellets |
| Comparative example 4 | Sodium polyacrylate | SPA | — | 2,821,200~3,761,600 | 0.5000 | 0.007 |

TABLE 2

|  | Types of additives | | Charge density [meq/g] | Molecular weight | Concentration of additive [%(w/v)] | Filamentous fungal pellet density [g-dry cell/cm$^3$] |
|---|---|---|---|---|---|---|
| Example 16 | Cationized polyvinyl alcohol | C-PVA | 8.23 | 78,000~86,000 | 0.0045 | 0.047 |
| Comparative example 5 | No additive | — | — | — | — | 0.018 |

As evident from Table 1 and Table 2, the filamentous fungal pellets prepared in Examples 1 to 16 had a higher mycelial density as compared with the filamentous fungal pellets in Comparative examples 1 to 5.

Example 17

<Preparation of Filamentous Fungal Pellet>
[Preparation of Spore Suspension]

The spore suspension was prepared by a similar manner to that in Example 1 described above.

[Pelletization of Filamentous Fungus]

The filamentous fungal pellet was prepared through the following two-stage culturing. The first stage culturing is a step of spore germination and pelletization, and the second stage culturing is a step of pellet propagation.

In the first stage culturing, a PDB medium serving as a pellet-formation medium was placed in a 30 L aeration and agitation vessel (manufactured by Mitsuwa Frontech Corp.). After heat-sterilizing the vessel, heat-sterilized poly-allylamine (molecular weight 15,000, charge density 17.5, manufactured by Polysciences, Inc.) was added to the medium in an amount of 0.0015% (w/v), and the spore suspension was inoculated in the resulting medium in an amount of 1×10$^4$ spores/mL. The amount of the culture medium was adjusted to 15 L by adding sterile water, and culturing was performed for 3 days at a liquid temperature of 27° C., an agitation speed of 300 r/min, and an in-vessel pressure of 0.040 MPa under a condition in which DO is controlled at 1.0 ppm by supplying the air. Further, an anti-foaming sensor was used to perform a control so as to add an anti-foaming agent (1% KM-72F (manufactured by Shin-Etsu Chemical Co., Ltd.)) upon foaming.

In the second stage culturing, a supernatant of the culture medium was first removed from the 30 L aeration and agitation vessel through a metal filter with an opening of 250 m installed in the vessel while pressurizing the inside of the vessel. Subsequently, a sterilized propagation medium was placed in the vessel and sterilized distilled water was added thereto to give 15 L of the liquid amount in the vessel. Each compound was added to the medium at the following medium concentration. Medium concentrations: glucose (manufactured by Wako Pure Chemical Industries, Ltd.) 6% (w/v), magnesium sulfate heptahydrate 0.025% (w/v), zinc sulfate heptahydrate 0.009% (w/v), ammonium sulfate 0.1% (w/v), and potassium dihydrogen phosphate 0.06% (w/v). Culturing was performed at 27° C. for 12 hours at an agitation speed of 300 r/min and an in-vessel pressure of 0.040 MPa under a condition in which DO is controlled at 2 ppm by supplying the air. The pH during culturing was maintained at 4 by appropriately adding 7 N sodium hydroxide. Further, similar to the first stage culturing, a control was performed so as to add an anti-foaming agent (1% KM-72F) upon foaming.

[Collection of Pellet]

The filamentous fungal pellet culture medium obtained by the above operations was filtered with a nylon mesh filter for several tens of seconds until filtrate dripping was stopped to obtain the wet filamentous fungal pellet. The pellet obtained in the second stage was immediately subjected to evaluation of fermentability. A portion of the filamentous fungal pellet was washed by a similar manner to that in Example 1 described above and then used for calculating the filamentous fungal pellet density [g-dry cell/cm$^3$].

<Evaluation of Productivity of Fumaric Acid and Ethanol>
[Culture Method]

A sterilized medium and the filamentous fungal pellet thus prepared (in a wet state) were added in a sterilized 1 L aeration and agitation vessel, and then sterilized distilled water was added to provide 500 mL of the liquid amount. The medium in this culture was composed of 10% (w/v) glucose (manufactured by Wako Pure Chemical Industries, Ltd.), 0.025% (w/v) magnesium sulfate heptahydrate, 0.009% (w/v) zinc sulfate heptahydrate, 0.1% (w/v) ammonium sulfate, and water as the remainder. A volume occupied by the filamentous fungal pellet with respect to the medium was adjusted to 36 volt. Immediately after that, a 0-hour culturing sample was taken, and then culturing was performed at 35° C. and at a mixing speed of 500 r/min under a condition in which high concentration oxygen (>90%) was supplied at an aeration rate of from 0.3 to 1.0 vvm. Subsequently, culturing was continued for 5 hours while samples were taken over time. The pH (35° C.) was maintained at 4 by appropriately adding a 7 N sodium hydroxide solution.

[Measurement of Various Components by High Performance Liquid Chromatography (HPLC)]

The fermented liquid thus sampled was filtered using a cellulose acetate-made membrane filter having a pore diameter of 0.20 μm (manufactured by Advantec MFS) and then appropriately diluted with a 0.0085 N sulfuric acid aqueous solution to prepare a sample for HPLC analysis. HPLC analysis conditions are as follows.

Column: ICSep ICE-ION-300
Eluent: 0.0085 N sulfuric acid, 0.4 mL/min
Detection method: RI (HITACHI, ltd., L-2490)
Column temperature: 40° C.
Injection amount: 20 μL
Retention time: 40 min The retention time of each component in this analysis system is as follows.

Glucose: 16 min
Fumaric acid: 26 min
Ethanol: 34 min

[Calculation of Production Rate]

On the basis of analysis values of the fermented liquid, the following three items were evaluated: (1) consumption rate of saccharide (P[g/L/h]), (2) production rate of fumaric acid (Q [g/L/h]), and (3) production rate of ethanol (R [g/L/h]). The concentration [g/L] of each component was obtained from the HPLC analysis result and the rates were calculated by the following Formulas (1) to (3).

Evaluation results of Example 17 and Comparative example 6 are shown in Table 3. Note that, in the results, rates for 5 hours from the start to the end of culturing were adopted.

TABLE 3

| | Types of additives | | Charge density [meq/g] | Molecular weight | Concentration of additive [%(w/v)] | Filamentous fungal pellet density [g-dry cell/cm$^3$] | Glucose consumption rate [g/L/h] | Fumaric acid production rate [g/L/h] | Ethanol production rate [g/L/h] |
|---|---|---|---|---|---|---|---|---|---|
| Example 17 | Poly-allylamine | PAAm | 17.5 | 15,000 | 0.0015 | 0.213 | 18 | 3 | 3.5 |
| Comparative example 6 | Sorbitan monolaurate | SP-L10 | — | 346.46 | 0.5000 | 0.037 | 4.9 | 0.98 | 0.47 |

Consumption Rate of Saccharide $$P[g/L/h]=(G_0-G)/T \quad (1)$$

Production Rate of Fumaric Acid $$Q[g/L/h]=(F-F_0)/T \quad (2)$$

Production Rate of Ethanol $$R[g/L/h]=(E-E_0)/T \quad (3)$$

(In these Formulas, $G_0$, $F_0$, and $E_0$ represent a glucose concentration, a fumaric acid concentration, and an ethanol concentration, respectively, at 0-hour culturing; G, F, and E represent a glucose concentration, a fumaric acid concentration, and an ethanol concentration, respectively, after culturing; and T represents a fermentation time (h).)

Comparative Example 6

<Preparation of Filamentous Fungal Pellet>
[Preparation of Spore Suspension]

The spore suspension was prepared by a similar manner to that in Example 1 described above.
[Pelletization of Filamentous Fungus]

The filamentous fungal pellet was prepared through the following two-stage culturing.

In the first stage culturing, 0.5% (w/v) sorbitan monolaurate, a PDB medium, and 0.5% (w/v) sorbitan monolaurate were placed in a 30 L aeration and agitation vessel (manufactured by Mitsuwa Frontech Corp.). After heat-sterilizing the vessel, the spore suspension was inoculated in an amount of 1×10$^4$ spores/mL. Sterile water was added thereto to adjust the liquid amount of medium to 15 mL, and culturing was performed for 3 days at a liquid temperature of 27° C., an agitation speed of 300 r/min, and an in-vessel pressure of 0.040 MPa under a condition in which DO is controlled at 1.0 ppm by supplying the air. Further, an anti-foaming sensor was used to perform a control so as to add an anti-foaming agent (1% KM-72F (manufactured by Shin-Etsu Chemical Co., Ltd.)) upon foaming.

The second stage culturing was performed by a similar manner to that in Example 17.
[Collection of Pellet]

After completing the culturing, the wet filamentous fungal pellet was obtained by a similar manner to that in Example 17 described above and immediately subjected to evaluation of fermentability. A portion of the filamentous fungal pellet was used for calculating the filamentous fungal pellet density [g-dry cell/cm$^3$].
<Evaluation of Productivity of Fumaric Acid and Ethanol>

A similar manner to that in Example 17 described above was employed.

As evident from Table 3, it was confirmed that the production rates of fumaric acid and ethanol could be improved by using the filamentous fungal pellet having a high mycelial density of the present invention.

The invention claimed is:

1. A method for producing a filamentous fungal pellet, comprising a step of germinating spores of a filamentous fungus in a culture medium containing a cationic polymer, wherein the filamentous fungus is a fungus belonging to the genus *Rhizopus* or a fungus belonging to the genus *Trichoderma*, and
   wherein the filamentous fungal pellet has a density of from 0.1 g-dry cell/cm$^3$ to 0.3 g-dry cell/cm$^3$.

2. The method for producing the filamentous fungal pellet according to claim 1, wherein the content of the cationic polymer in the culture medium is 0.0001% (w/v) or more and 2% (w/v) or less.

3. The method for producing the filamentous fungal pellet according to claim 1, wherein the charge density of the cationic polymer is 0.1 meq/g or more and 100 meq/g or less.

4. The method for producing the filamentous fungal pellet according to claim 1, wherein the weight-average molecular weight of the cationic polymer is 1,000 or more and 1,000,000 or less.

5. The method for producing the filamentous fungal pellet according to claim 1, further comprising a step of propagating the filamentous fungal pellet in a culture medium different from the culture medium in the step of germinating the spores of the filamentous fungus.

6. The method for producing the filamentous fungal pellet according to claim 1, wherein the cationic polymer is one or more selected from the group consisting of poly-allylamine or a salt thereof, methyl glycol chitosan, a poly-diallyldialkyl ammonium salt, polyethylenimine, and a cationized polyvinyl alcohol.

7. The method for producing the filamentous fungal pellet according to claim 1, wherein the cationic polymer is one or more selected from the group consisting of poly-allylamine or a salt thereof, methyl glycol chitosan, a poly-diallyldialkyl ammonium salt, and a cationized polyvinyl alcohol.

8. The method for producing the filamentous fungal pellet according to claim 1, wherein the initial pH of the culture medium containing the cationic polymer is from 2 to 7.

9. The method for producing the filamentous fungal pellet according to claim 1, wherein the charge density of the cationic polymer is 2 meq/g to 30 meq/g or less.

10. The method for producing the filamentous fungal pellet according to claim 1, wherein the content of the cationic polymer in the culture medium is 0.0015% (w/v) or more and 2% (w/v) or less.

11. The method for producing the filamentous fungal pellet according to claim 1, wherein the cationic polymer is selected from the group consisting of polyethylenimine, poly-allylamine, allylamine salt polymer, poly-diallylamine, diallylamine salt polymer, methyl glycol chitosan, diallyldialkyl ammonium salt polymer, diallyldialkyl ammonium ethyl sulfate salt polymer and a cationized polyvinyl alcohol.

12. The method for producing the filamentous fungal pellet according to claim 1, wherein the weight-average molecular weight of the cationic polymer is 1,600 or more and 200,000 or less.

* * * * *